United States Patent [19]
Fischer

[11] Patent Number: 5,853,661
[45] Date of Patent: Dec. 29, 1998

[54] HIGH GOLD CONTENT BIO—COMPATIBLE DENTAL ALLOY

[75] Inventor: Jens Fischer, Kirchlindach, Switzerland

[73] Assignee: Cendres ET Metaux SA, Biel, Switzerland

[21] Appl. No.: 772,896

[22] Filed: Dec. 24, 1996

Related U.S. Application Data

[63] Continuation-in-part of Ser. No. 496,416, Jun. 29, 1995, abandoned.

[30] Foreign Application Priority Data

Jul. 5, 1994 [EP] European Pat. Off. .............. 94810394

[51] Int. Cl.[6] ..................................................... C22C 5/02
[52] U.S. Cl. ......................... 420/507; 420/510; 420/511; 148/430; 433/200.1; 433/207
[58] Field of Search ..................................... 420/507, 508, 420/509, 510, 511, 512; 148/405, 430, 678, 538; 433/200.1, 207; C22C 5/02

[56] References Cited

U.S. PATENT DOCUMENTS

| | | |
|---|---|---|
| 3,196,536 | 7/1965 | Knippenberg et al. . |
| 4,606,981 | 8/1986 | Mizuhara . |

FOREIGN PATENT DOCUMENTS

| | | |
|---|---|---|
| 190648 | 8/1986 | European Pat. Off. . |
| 2643649 | 8/1990 | France . |
| 2052749 | 5/1972 | Germany . |
| 2302837 | 8/1974 | Germany . |
| 2357552 | 5/1975 | Germany . |
| 2424575 | 12/1975 | Germany . |
| 3502914 | 7/1986 | Germany . |
| 4419408 | 6/1994 | Germany . |
| 62-248595 | 10/1987 | Japan . |
| 5-70252 | 3/1993 | Japan . |
| 9200564 | 10/1993 | Netherlands . |

OTHER PUBLICATIONS

J. Wirz, "Schadigung des Paradontes durch zahnarztliche Werkstoffe", ZWR, 102, Jan. 1993, pp. 146–162.
"Dental Ceramic fused to metal restorative materials", International Standard, ISO 9693, First Edition, Jun. 1, 1991.
CA 105:157445, 1986.
CA 114:127321 1990.
WPI Abs 74–570IIV[32]of DE 2302837, 1975.
Chem Abs. 125: 230887, 1996.

*Primary Examiner*—Margery Phipps
*Attorney, Agent, or Firm*—Foley & Lardner

[57] ABSTRACT

A high gold content dental alloy comprises, on a weight basis, 91 to 99.4% of gold, 0.5 to 3% of at least one metal selected from titanium and tantalum, up to 5% of silver, 0.05 to 1% of iridium and/or tungsten, and up to 1% at least one element selected from the group comprising rhodium, ruthenium, platinum, osmium, iron, molybdenum, niobium and rhenium.

23 Claims, No Drawings

HIGH GOLD CONTENT BIO— COMPATIBLE DENTAL ALLOY

CROSS REFERENCE TO APPLICATIONS

This is a continuation-in-part of U.S. patent application Ser. No. 08/496,416, filed Jun. 29, 1995, now abandoned.

BACKGROUND OF THE INVENTION

1. Field of the Invention

The present invention relates to a dental alloy. More specifically, the present invention relates to a new and useful dental alloy having a high gold content and a natural golden yellow color, for facing commercially available dental ceramic compounds or the manufacture of dental prosthesis parts which either remain unfaced or are faced with synthetic or other materials.

2. Discussion of the Related Art

Noble metal dental alloys having a high gold content are widely used in metallic, solidly fastened dentures such as crowns, bridges, etc., inter alia, due to their high biological compatibility and corrosion resistance in the oral milieu. Furthermore, these alloys are technically easy to work with.

Silver and copper containing gold casting alloys have been successfully used for a long time in restorative dentistry. In conventional alloys, the high mechanical resistance required when these materials are to be faced with synthetic materials is adjusted through the silver to copper ratio.

In view of the aesthetics necessary of solidly fastened dental reconstructions, especially in the visible region, an at least partial facing of a metallic base by a ceramic compound has proven to be particularly useful since the advantages of the ceramics, namely hardness, aesthetics and outstanding biological compatibility, can optimally be combined with the advantages of the metallic material, namely tensile strength and more precise fit.

The use of a ceramic facing requires that the alloy possess special properties. The melting point of the alloy should be markedly higher than the baking temperature of the ceramics, which is about 980° C., and the alloy must furthermore exhibit a thermal stability which enables the metallic base to be faced while remaining dimensionally stable during the heating or baking operation.

In order to guarantee a durable adhesion between the alloy and the ceramics, tensile stress should not be allowed to build up during the manufacturing process. This stress prevention is achieved, in an already known manner, by selecting the thermal expansion coefficient of the alloy to be slightly higher than that of the ceramics. During the cooling process, a compressive strain is produced in the ceramic coating due to the slightly greater contraction exhibited by the alloy.

The above requirements have resulted in the development of special burn-on alloys which are grouped in a class separate from the conventional gold casting alloys and which are controlled by the standards ISO 9693 and DIN 13927.

In order to achieve the above discussed required burn-on alloy properties, platinum and/or palladium have been added to the gold based alloys intended for metal-ceramic use. Furthermore, metals other than noble metals, such as copper, indium, gallium, tin and/or zinc, are added in order to improve the strength of the alloy. The alloy strength can be improved by adding higher proportions of silver and copper. However, this renders the alloy susceptible to oxidation and tends to lead to undesired reactions between such alloys and the associated ceramic.

In particular, additions of either palladium or platinum lead to a perceptible reduction of the desired natural yellow color of the alloy which is considered by the patient as being aesthetically agreeable and desirable.

Recently, some non-noble metals which are used in the noble metal alloys have been suspected of causing problems and pathological reactions in some patients. Reference is especially made to indium which is contained in nearly all burn-on alloys; see the article of J. Wirz: "Schadigung des Paradontes durch zahnarztliche Werkstoffe" (Damage of the paradontium by dental materials), Zahnarztliche Welt 102, 146 (1993). Palladium is also suspected of provoking toxic or allergic reactions if it is contained in higher proportions in the noble metal alloy and is capable of being liberated by corrosion.

Furthermore, the need for a universally applicable dental alloy is becoming of ever increasing importance, i.e. a dental alloy which is suitable both for conventional dental prostheses which either remain unfaced or are faced with synthetic material, respectively, and for metal-ceramic production. Such alloys have the advantage of preventing the formation of a galvanic system due to the use of different alloys in the mouth cavity and associated corrosion processes.

Recently, such universal alloys have been proposed which are based on Au—Ag—Pt—cu with the addition of the non-noble metals such as indium and zinc. However, these alloys suffer from the shortcoming that they are relatively Susceptible to corrosion. This susceptibility is particularly due to the presence of surface oxides which are formed during thermal treatment (burning), which are not necessarily covered by the ceramic in the region of the crown edges, and which are therefore exposed to saliva and its corrosive action. Furthermore, a special, low melting ceramic is required for this alloy and which, depending on the manufacturing method, presents a higher corrosion rate than the known higher melting facing ceramics.

In addition, alloys of high gold content generally have an inferior high temperature creep resistance so that metallic, long span bridge structures are generally deformed during the burning process and lose their precision fit. Therefore, long bridges which are to be faced with ceramic must be made from alloys having a high palladium content, and therefore do not retain the desired natural gold color and further present the biological drawbacks mentioned above.

On the other hand, the non-noble metals titanium and tantalum have proven to be highly biologically compatible dental materials. For example, implants of titanium will heal in the bone without any defense reaction due to the superficial formation of titanium oxide which is very corrosion resistant and inert, and allergic reactions to this material are extremely rare if not non-existent. Therefore, these metals are viable from a clinical and biological perspective as being ideal alloy partners for gold which is also known to be extremely corrosion resistant.

Titanium containing dental alloys of high gold content which are suited for the facing with ceramics are already known. DE-A-2,302,837 discloses a titanium alloy of high gold content which further contains a relative high proportion of platinum or a metal of the platinum group as well as palladium which may provoke, as already described above, allergic reactions. Furthermore, DE-A-2,357,552 describes a titanium alloy or high gold content which also contains an element of the platinum group, but no quantitative indications relating to this alloy are given.

In addition, titanium alloys of high gold content for the use in jewelry are known, for example from EP-A-0,190, 648. However, these ornamental alloys must comply with other criteria than those demanded by dental alloys, and compositions of ornamental alloys cannot therefore be readily used as dental alloys.

SUMMARY OF THE INVENTION

It is a primary object of the present invention to provide a new and useful dental alloy which not only exhibits an outstanding biological compatibility but also can be universally used for a wide range of dental applications.

It is another object of the invention to provide a dental alloy which meets the ISO 1562 and ISO 9693 standards as well as those of DIN 13927.

A further object of the invention is to provide a dental alloy having a high gold content and which possess, in spite of other metals alloyed therewith, a pleasant natural yellow color which is optimally close to that of genuine gold.

The objects are attained by a high gold content dental alloy which in accordance with the invention comprises, on a weight basis, 91 to 99.4% of gold, 0.5 to 3% of at least one metal selected from titanium and tantalum, up to 5% of silver, 0.05 to 1.0% of iridium and/or tungsten, and up to 1% of at least one element selected from the group comprising rhodium, ruthenium, platinum, osmium, iron, molybdenum, niobium and rhenium.

An alloy which is particularly suited for the dental applications of the nature indicated above, contains 91.0 to 99.4% of gold, 1.4 to 2.4% of titanium and a mixture of iridium and tungsten. The amount of each iridium and tungsten range from 0.05 to 1.0%. More preferably, the amounts of iridium and tungsten are each in the range of 0.05–0.15%.

Another alloy which is particularly suited for the intended purposes of this invention comprises 97.5 to 98.5% of gold, 1.4 to 2.4% of titanium and 0.05 to 1% iridium. A more preferable range of iridium in this alloy is 0.05 to 0.15%. Silver may also be included in this alloy in an amount of up to 5%.

A further alloy which meets the above objects comprises 97.5 to 98.5% of gold, 1.4 to 2.4% of titanium and 0.05 to 1.0% of iridium and/or tungsten. A more preferable range of tungsten in this alloy is 0.05–0.15%. This alloy may also contain silver in an amount of up to 5%.

DETAILED DESCRIPTION OF THE INVENTION

Tests have shown that an alloy composed of 91 to 99.4% gold, 0.5 to 3% of titanium and/or tantalum, amounts of silver up to 5% and amounts of at least one of iridium, rhodium, ruthenium, platinum, palladium, osmium, tungsten, iron, molybdenum, niobium and/or rhenium in an amount up to 1%, surprisingly presents universal properties and can therefore also be used in conventional techniques; the alloy fulfills the requirements of the standards ISO 1652 and ISO 9693 and of DIN 13927 as well. Further, as gold as well as titanium exhibit extremely good biological compatibility, an alloy containing these two components is also extremely biologically compatible and is furthermore very attractive from an aesthetic viewpoint since titanium or tantalum do not perceivably influence the golden color. Furthermore, since this alloy contains only a very small proportion of non-noble metals it maintains its high corrosion resistance.

Furthermore, it has surprisingly been found that alloys having the above-mentioned composition display a very good high temperature creep resistance. For example, an alloy having the following composition: 97.5 to 98.5% of gold, 1.4 to 2.4% of titanium, and 0.05 to 0.15% of iridium has a high temperature creep resistance which is better than all of the noble metal casting alloys used so far in the dental field. For the first time, this alloy allows ceramic facing of long metallic bridge structures which are cast from a golden yellow alloy of a high gold content. It has been found that on the addition of more than 1% of platinum to this alloy, as has been described in DE-A-2,302,837, for example, the high temperature creep resistance is markedly reduced.

It should be noted that the pure binary gold-titanium (AuTi) alloy solidifies 60 as to be very dendritic and to have a very course grain. These properties Undesirable due to the increased corrodibility and the inhomogeneous properties which result from such course grains. For this reason high-melting elements are alloyed with precious (noble) metals in small quantities (promilles). These high melting elements either do not fuse during the melting and pouring process, or are the first component to solidity during solidification.

In this way, the additions act as crystallization nuclei and thus refine the grain. Iridium is a usual refining agent in high gold containing alloys for dental castings. This metal acts in the AuTi alloy as a grain refiner, however, it does not achieve the same level of grain refinement as is possible with known gold-platinum dental alloys. Tungsten, on the other hand, has been found to produce better grain refining characteristics than iridiwu, however, during the baking process an undesired increase of the granular size can occur. Accordingly, with a combination of iridium and tungsten, the combined grain refining effect of tungsten and the granular size stabilization of iridium are achieved. This results in a fine grain which imparts a high corrosion resistance on the alloy.

Therefore, a further alloy which, in accordance with the present invention is highly suited to dental use, features a Composition of 97.5 to 98.5% gold, 1.4 to 2.4% titanium, 0.05 to 1.0% iridium, more preferably 0.4 to 0.6% iridium; or 0.05 to 1.0 % tungsten, more preferably 0.05–0.15% tungsten; or a combination of 0.05 to 1.0% iridium with 0.05–1% tungsten, preferably 0.05–0.15% of each iridium and tungsten.

Although the present invention has been described with reference to only a limited number of examples, the various changes and modifications, such as the inclusion of up to 5% of silver and/or 0.5 to 3.0% of tantalum, for example, which can be made without departing from the scope of the invention, which is defined only by the appended claims, will be apparent to those skilled in the art to which the present invention pertains.

What is claimed is:

1. A bio-compatible dental alloy of high gold content comprising, by weight, from 91 to 99.4% of gold, from 0.5 to 3% of at least one metal selected from the group consisting of titanium and tantalum, and an effective amount of tungsten to provide grain refinement, and 0–1% platinum.

2. A bio-compatible dental alloy of high gold content according to claim 1, comprising 0.05 to 1.0% of tungsten.

3. A bio-compatible dental alloy of high gold content according to claim 1, comprising 0.05 to 0.15% of tungsten.

4. A bio-compatible dental alloy of high gold content comprising, by weight, from 91 to 99.4% of gold, from 0.5 to 3% of at least one metal selected from the group consisting of titanium and tantalum, and a mixture of iridium and an effective amount of tungsten to provide grain refinement, and 0–1% platinum.

5. A dental alloy of high gold content, consisting of from 91 to 99.4% of gold, from 0.5 to 3% of at least one metal selected from the group consisting of titanium and tantalum, from 0 to 5% of silver, from 0.05 to 1%. of tungsten, and up to 1% of at least one metal selected from the group consisting of iridium, rhodium, ruthenium, platinum, palladium, osmium, iron, molybdenum, niobium and rhenium, the percentages given being by weight, and wherein said dental alloy is bio-compatible.

6. A dental alloy as set forth in claim 5, wherein said titanium is contained in an amount of 1.4 to 2.4%.

7. A dental alloy of high gold content, consisting of from 91 to 99.4% of gold, from 0.5 to 3% of at least one metal selected from the group consisting of titanium and tantalum, from 0 to 5% of silver, from 0.05 to 1% of iridium, 0.05 to 1% tungsten, and up to 1% of at least one metal selected from the group consisting of rhodium, ruthenium, platinum, palladium, osmium, iron, molybdenum, niobium and rhenium, the percentages given being by weight, and wherein said dental alloy is bio-compatible.

8. A dental alloy as set forth in claim 7, wherein said titanium is contained in an amount of 1.4 to 2.4%.

9. A bio-compatible dental alloy of high gold content comprising, by weight, from 97.5 to 98.5% of gold, from 1.4 to 2.4% of titanium, and a mixture of iridium and an effective amount of tungsten to provide grain refinement.

10. A bio-compatible dental alloy of high gold content as set forth in claim 9, further comprising silver in an amount up to 5%.

11. A bio-compatible dental alloy of high gold content as set forth in claim 9, further comprising 0.5 to 3% of tantalum.

12. A dental alloy of high gold content as set forth in claim comprising 0.05 to 1.0% of iridium and 0.05 to 1% of tungsten.

13. A dental alloy of high gold content as set forth in claim 9, comprising 0.05 to 0.15% of iridium and 0.05 to 0.15% of tungsten.

14. A bio-compatible dental alloy of high gold content consisting of, by weight, from 97.5 to 98.5% of gold, from 1.4 to 2.4% of titanium, 0 to 5% silver, from 0.05 to 1.0% of iridium and from 0.05 to 1.0% of tungsten.

15. A bio-compatible dental alloy of high gold content as set forth in claim 14, wherein the iridium and/or tungsten is contained in a range of 0.05 to 0.15%.

16. A dental alloy of high gold content, consisting of from 91 to 99.4% of gold, from 0.5 to 3% of at least one metal selected from the group consisting of titanium and tantalum, from 0 to 5% of silver, from 0.05 to 1% of tungsten, from 0 to 1% of iridium, and up to 1% of one or more metals selected from the group consisting of rhodium, ruthenium, platinum, palladium, osmium, iron, molybdenum, niobium, and rhenium, the percentages given being by weight, and wherein said dental alloy is bio-compatible.

17. A dental alloy of high gold content as set forth in claim 16, including said iridium.

18. A dental alloy of high gold content as set forth in claim 16, including from 0.05 to 0.15% of iridium.

19. A dental alloy of high gold content comprising from 91 to 99.4% of gold, from 0.5 to 3% of at least one metal selected from the group consisting of titanium and tantalum, from 0 to 5% of silver, and an effective amount of tungsten to provide grain refinement up to 1%, the percentages given being by weight, and wherein said dental alloy is bio-compatible.

20. A dental alloy of high gold content as set forth in claim 19, further comprising iridium, wherein the iridium is present, and is present in an amount up to 1% by weight.

21. A dental alloy of high gold content, comprising from 91 to 99.4% of gold, from 0.5 to 3% of at least one metal selected from the group consisting of titanium and tantalum, from 0 to 5% of silver, from 0.05 to 1% of tungsten, from 0 to 1% of iridium, and up to 1% of one or more metals selected from the group consisting of rhodium, ruthenium, platinum, palladium, osmium, iron, molybdenum, niobium, and rhenium, the percentages given being by weight, and wherein said dental alloy is bio-compatible.

22. A dental alloy of high gold content as set forth in claim 21, wherein said iridium is present.

23. A dental alloy of high gold content as set forth in claim 21, which comprises 0.05 to 1% of iridium.

* * * * *

UNITED STATES PATENT AND TRADEMARK OFFICE
CERTIFICATE OF CORRECTION

PATENT NO. : 5,853,661
DATED : December 29, 1998
INVENTOR(S) : Dr. Jens Fischer

It is certified that error appears in the above-identified patent and that said Letters Patent is hereby corrected as shown below:

Column 5, Claim 12, line 1 "set forth in claim" should read --set forth in claim 9--.

Signed and Sealed this

Ninth Day of November, 1999

Attest:

Q. TODD DICKINSON

Attesting Officer

Acting Commissioner of Patents and Trademarks